United States Patent [19]

Johnson

[11] 4,294,866
[45] Oct. 13, 1981

[54] METHOD FOR PRODUCING MONOCELLULAR LAYERS OF CELL-CONTAINING BIOLOGICAL FLUID

[75] Inventor: Leighton C. Johnson, Edwardsburg, Mich.

[73] Assignee: Miles Laboratories, Inc., Elkhart, Ind.

[21] Appl. No.: 204,564

[22] Filed: Nov. 6, 1980

[51] Int. Cl.³ .............................................. B44D 1/02
[52] U.S. Cl. ......................................... 427/2; 424/3
[58] Field of Search ................... 118/52; 427/2; 424/3

[56] References Cited
U.S. PATENT DOCUMENTS 3,705,048 12/1972 Staunton ................................ 427/2

*Primary Examiner*—Sam Silverberg
*Attorney, Agent, or Firm*—Joseph C. Schwalbach

[57] ABSTRACT

An improved method is provided for producing monocellular layers of cell-containing biological fluid, such as blood, by spinning a sample slide bearing a sample to be analyzed. In the practice of the improved method, the slide is positioned with the sample-bearing surface thereof facing downwardly so that the force of gravity aids, rather than hinders, monocellular layer formation. Such layer formation is further facilitated by spinning of the slide in a holder provided with integral wall means shielding the sample from the buffeting effect of circumambient air to thereby avoid premature drying of the sample, minimize cell distortion and prevent aerosol formation.

13 Claims, 4 Drawing Figures

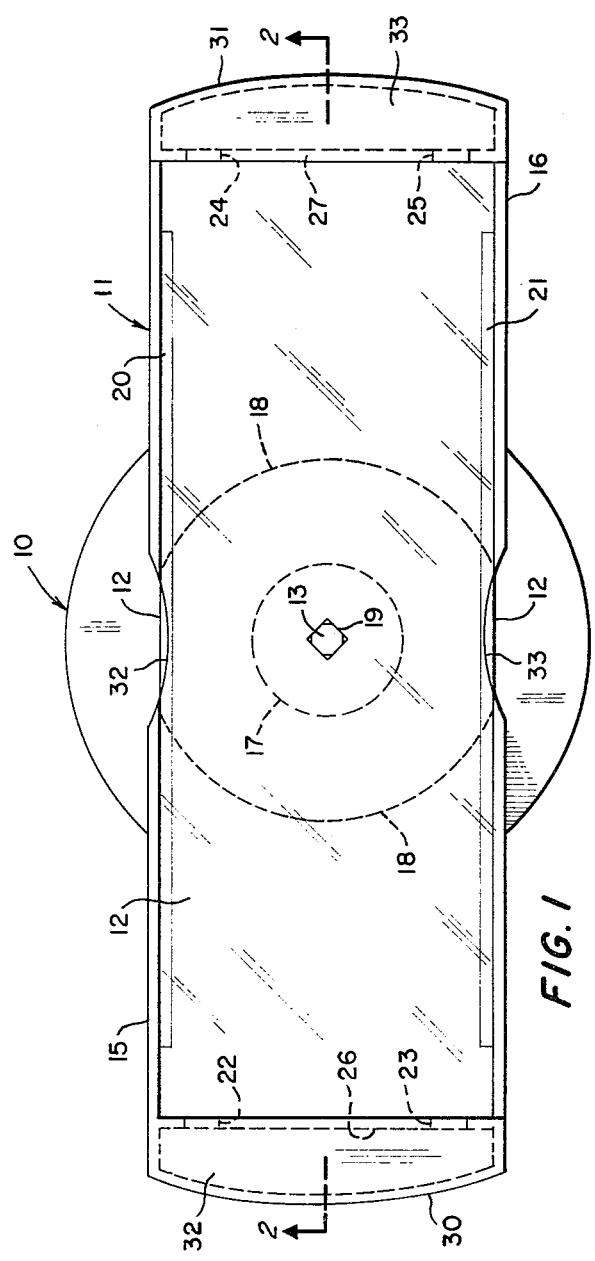
FIG. 1
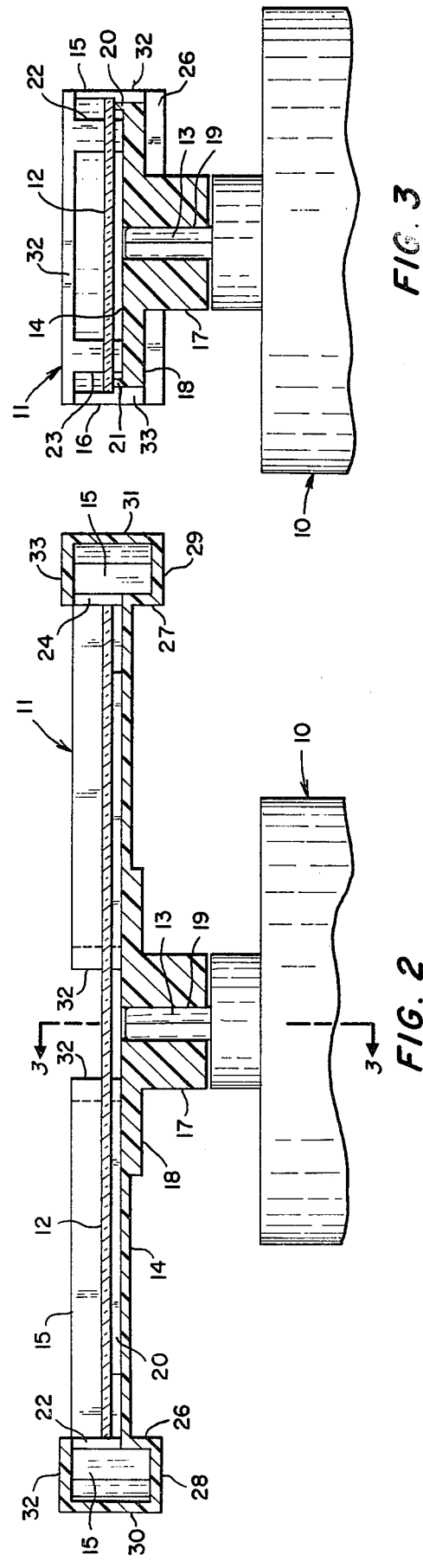
FIG. 2
FIG. 3

METHOD FOR PRODUCING MONOCELLULAR LAYERS OF CELL-CONTAINING BIOLOGICAL FLUID

This application is a division, of application Ser. No. 122,121, filed Feb. 19, 1980.

BACKGROUND OF THE INVENTION

This invention relates to an improved method for producing monocellular layers of cell-containing fluids, such as blood, to be analyzed by differential counting of the cells in the monolayer. More particularly, the invention relates to an improved method wherein production of a high quality monolayer is facilitated and cell distortion is minimized by spinning of a slide with the fluid sample-bearing surface thereof facing downwardly and while in a holder having integral means for shielding the sample from the buffeting effects of air currents normally generated by such spinning.

With the advent of widespread use of Automated Differential Cell counting techniques as an aid in the diagnosis of disease, various instruments have been developed for preparing the monocellular layers of biological fluids, such as blood, which are preferred for such analysis. The preparation of blood specimens by the "spinner" method to produce a generally monocellular layer of blood on a slide and prior art apparatus for practicing such methods are discussed in the following publications:

Ingram, M. and Minter, F. M.: Semiautomatic Preparation of Coverglass Blood Smears Using a Centrifugal Device, Am. J. Clin. Path., 51:214-221, 1969.

Bacus, J. W.: Erythrocyte Morphology and Centrifugal "Spinner" Blood Film Preparations, J. Histochem. Cytochem., 22: 506-516, 1974.

Wenk, R. E.: Comparison of Five Methods of Preparing Blood Smears, AJMT, 42: 71-78, 1976.

Nourbakhsh, M., Atwood, J. G., Raccio, J. and Seligson, D.: An Evaluation of Blood Smears Made by a New Method Using a Spinner and Diluted Blood, AJCP, 70: 885-892, 1978.

Various problems have been encountered in the preparation of monocellular layers of blood. One such problem is that of wide variations in the differential count depending upon where in the layer of smear the count is taken. U.S. Pat. No. 3,577,267, issued to Preston, et al. on May 4, 1971, discloses a method by which, it is stated, a uniform monolayer of flattened undamaged cells is produced. By this method, a sample-bearing slide is spun at a speed in a range of from 4,000 to 10,000 rpm for a few tenths of a second after acceleration to that range within less than ten milliseconds. Producing such acceleration, and, of course, the deceleration necessary to limit the spinning to the precise fractional second period, required a relatively high powered, heavy motor, flywheel and clutching/braking mechanism, and sophisticated time control equipment.

Another problem encountered in the preparation of monocellular layers is cell distortion resulting from the buffeting or shear effect of air currents set up by the spinning slide and holder therefor, and from resultant premature drying of the spun sample. U.S. Pat. No. 3,705,048, issued to Staunton on Dec. 5, 1972, discloses an apparatus, the objective of which is protection of the sample from undesirable buffeting and drying. In this patent the spinning slide and the holder therefor to which it is clamped are enclosed within a relatively close-fitting enclosure which reduces the amount of air which can contact the spinning sample by limiting such contact to the air within the enclosure.

Presently available apparatus for the preparation of monocellular layers is expensive, heavy, cumbersome and requires a blood sample, typically 100 microliters in volume, which must be obtained by venous puncture. The need for a blood sample of this size presents difficulties not presented where a much smaller size capillary blood sample, obtainable, for example, by a finger prick, will suffice. Obtaining a venous blood sample causes considerably more patient discomfort and requires considerably more time than does obtaining a capillary blood sample. Moreover, the requirement for a venous blood sample presents difficulties in pediatrics where infants have too little blood to spare for samples of such size.

SUMMARY OF THE INVENTION

With the foregoing in mind, it is an object of the present invention to provide an improved method for producing monocellular layers of cell-containing biological fluids, such as blood, for the use with automatic or manual cell counting procedures, in which layers the cells are uniformly distributed and distortion thereof is minimized.

Another object of the invention is to provide an improved method of the class described by which the desired monolayers can be produced from a small volume blood sample of the size obtainable from capillary sources, such as by a prick of a finger, ear lobe or heel.

A more specific object of the invention is to provide an improved method of the aforementioned character in which the fluid sample is applied to the slide by the wedge method prior to spinning.

Yet another object of the invention is to provide an improved method as aforedescribed by which high quality monolayers can be prepared without any requirement for rapid acceleration, precise spinning time or rapid deceleration of the spun slide, or need for elaborate or sophisticated control means.

Still another object of the invention is to provide an improved method of the aforementioned character in the practice of which the force of gravity aids in monolayer formation during spinning by virtue of disposition of the slide with the sample-bearing surface thereof facing downwardly during spinning thereof.

A further object of the invention is to provide an improved method as aforedescribed wherein monocellular layer formation is facilitated by spinning of the slide in a holder provided with integral wall means enclosing and protecting the sample-bearing surface of the slide to thereby protect the sample from the buffeting effect of air currents, premature drying and cell distortion, and at the same time advantageously avoiding any potential health hazard from contamination of the atmosphere by vaporization or aerosolization of the sample during spinning.

Still another object of the invention is to provide an improved method of the class described wherein excess sample fluid spun off from the slide during spinning is collected in well means forming part of the slide holder.

Other objects and advantages of the invention will become apparent as the description proceeds, reference being had to the drawing accompanying and forming a part of this specification.

BRIEF DESCRIPTION OF THE DRAWING

In the drawing, which illustrates one embodiment of the preferred form of apparatus for practicing the improved method and in which like characters of reference indicate the same parts in all of the views;

FIG. 1 is a plan view of the improved apparatus, a microscope slide being shown in operative position within the slide holder;

FIG. 2 is a vertical sectional view taken along the line 2—2 of FIG. 1;

FIG. 3 is a vertical sectional view taken along the line 3—3 of FIG. 2; and

DETAILED DESCRIPTION OF THE PREFERRED EMBODIMENT

Figure 4:
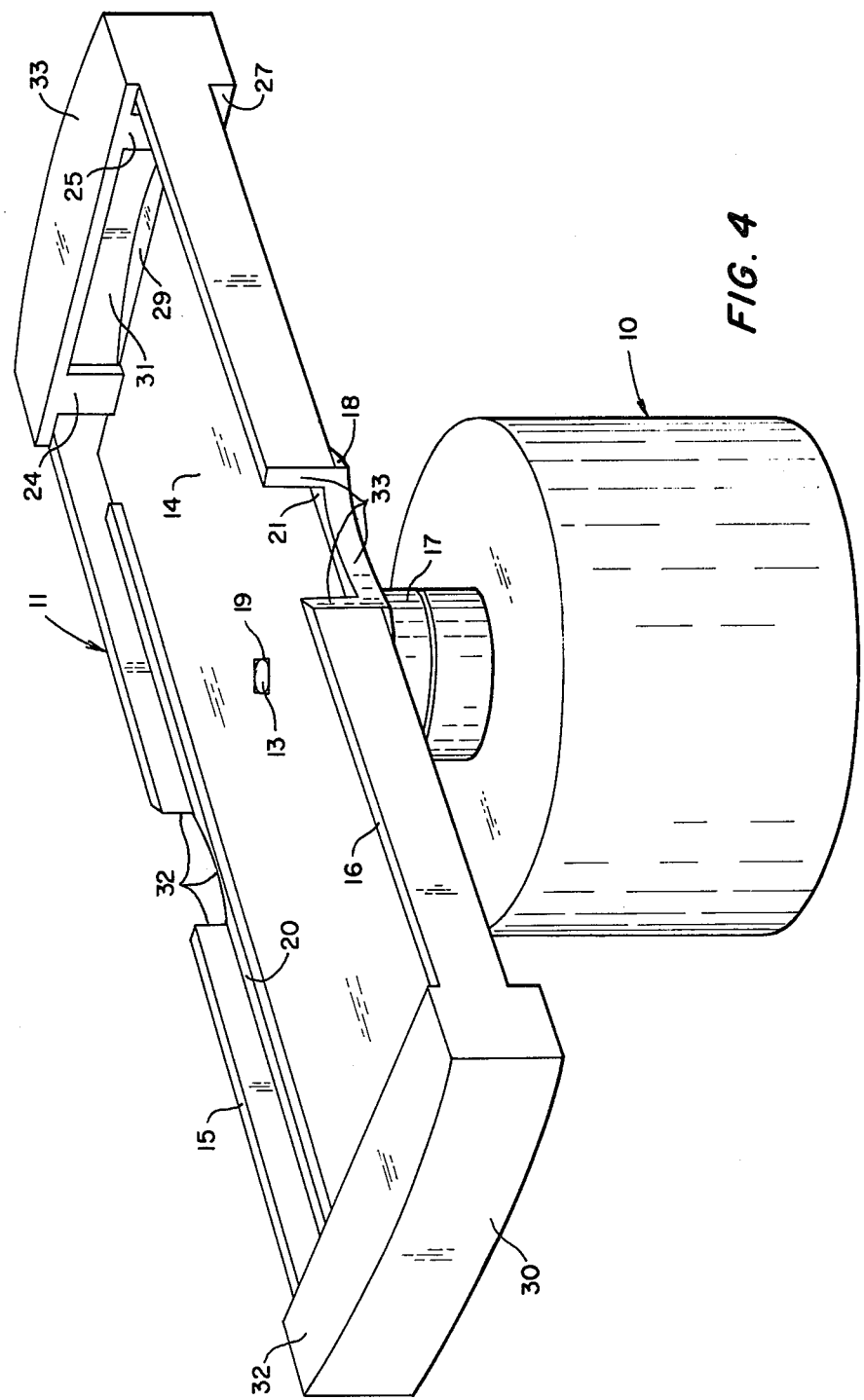
FIG. 4 is a perspective view of the improved apparatus.

Referring now to the drawing the improved apparatus comprises a motor 10, which is preferably electrically powered, and a slide holder 11, the latter being adapted to accommodate a slide, such as the microscope slide 12 shown in FIGS. 1 to 3. The motor 10 may be line powered, or it may be battery powered to facilitate portability of the apparatus. Motor 10 has a vertical drive shaft 13 which in the illustrated embodiment has an upper end portion of square cross-section.

The slide holder 11 is preferably molded of any suitable organoplastic material such as polystyrene, polycarbonate, ABS resin, and linear polyethylene, and is generally rectangular in plan view as shown in FIG. 1. Holder 11 has a rectangular horizontal bottom wall 14 and wall means in the form of upstanding parallel longitudinally extending side walls 15 and 16 which, with bottom wall 14, provide said holder and open-ended channel shape.

A cylindrical hub 17 depends centrally from the bottom wall 14, the latter being formed with a circular thickened portion 18 coaxial with said hub. The hub 17 is formed with a coaxial bore 19, the shape of which is complemental to that of motor shaft 13, i.e., square in the illustrated embodiment, so that holder 11 will be rotated by rotation of said shaft. The bore 19 may extend through the bottom wall 14 as shown, and the axis thereof preferably intersects the longitudinal and transverse center lines of bottom wall 14 as shown. The illustrated holder 11 has a readily manually releasable friction-fit on shaft 13; however, any other suitable releasable driving connection may be provided between the holder 11 and shaft 13.

The holder 11 is formed with first shoulder means adjacent the side and bottom walls thereof which, in the illustrated embodiment, take the form of rails 20 and 21 disposed at the junctures of bottom wall 14 with sidewalls 15 and 16, respectively, as shown. Rails 20 and 21 are adapted to support the slide 12 in spaced parallel relation to bottom wall 14 by engagement with longitudinal edge portions of the underside of said slide. A space of 1 millimeter between the slide 12 and bottom wall 14 has been found to be satisfactory. The first shoulder means can take suitable or desired forms other than those of rails 20 and 21.

The sidewalls 15 and 16 are contiguous with the opposite longitudinal edge portions of slide 12 and define the operative position thereof in a transverse direction within holder 11. Second shoulder means are provided for defining the operative position of the slide 12 in a longitudinal direction within holder 11. In the illustrated embodiment the second shoulder means take the form of upstanding spaced ribs 22 and 23 at one end of bottom wall 14 and corresponding ribs 24 and 25 at the opposite end thereof. The ribs 22 to 25 are contiguous with the opposite end edge portions of the slide 12 as shown. Thus, the slide 12, when in its operative or spinning position within the holder 11, is disposed normal to the rotational axis of the motor shaft 13 with the intersection of its longitudinal and transverse center lines intersected by said shaft axis.

The holder 11 is preferably provided at the open ends thereof with integral well means for receipt of excess fluid spun off the slide during monolayer formation. Such well means in the illustrated embodiment are formed by inner transverse vertical walls 26 and 27 depending from the outer ends of bottom wall 14, well bottom walls 28 and 29, arcuate outer vertical walls 30 and 31 and top walls 32 and 33. Holder side walls 15 and 16 extend beyond the ends of bottom wall 14 and provide side walls for both of the well means as shown.

In order to facilitate digital placement of a slide in operative position within and removal of a slide from the holder 11, said holder is formed with arcuate cutaway portions 32 and 33 in walls 15 and 16, rails 20 and 21 and the thickened bottom wall portion 18. As best shown in FIGS. 1 and 3, the cutaway portions 32 and 33 do not extend transversely all the way through the rails 20 and 21. Thus, when slide 12 is in operative position, the space within holder 11 below said slide is open to the exterior only at the outer ends of said holder.

In the practice of the improved method using the illustrated apparatus, a sample of biological fluid, for example a drop of blood obtained by a finger puncture, is deposited on a major surface of a clean glass microscope slide 12, near one end thereof and is spread over said slide following the well-known wedge technique by which the blood is drawn across the slide with the edge of a second glass slide. Such prespreading of the blood provides a relatively thick blood layer on the slide surface, yet requires a sample volume which is only about one-fifth that required for blood samples processed by conventional slide-spinning methods. i.e., 15 to 20 microliters vs. 70 to 100 microliters.

The slide 12 is then placed in the holder 11 in the operative position shown in FIGS. 2 and 3, with the sample-bearing surface thereof facing downwardly. The rails 20 and 21 support the slide 12 spaced above the bottom wall 14 of the holder 11 a distance sufficient so that the fluid sample (not shown) is held out of contact with said bottom wall, for example the 1millimeter distance aforementioned. The slide, when in operative position within the holder 11 is constrained from longitudinal and transverse movement within said holder by side walls 15 and 16 and upstanding ribs 22 to 25.

The motor is then operated to spin the holder 11 and slide 12 in a horizontal plane and generate centrifugal force sufficient to cause those portions of the sample not bound to the slide to flow outwardly and be spun off into the end wells of holder 11, leaving a thin monocellular layer (also not shown) of sample on the sample-bearing surface of the slide. In contrast to conventional spinning methods and apparatus, the speed of rotation and the duration of the spinning time in the improved method are not narrowly critical. It has been found that excellent monocellular layers can be prepared in the improved apparatus by spinning normal blood samples for about 5 seconds at about 5000 rpm. For higher viscosity specimens the spinning speed and/or the spinning time may advantageously be increased; whereas for lower viscosity specimens, such as from burn patients, the spinning speed and/or the spinning time may advantageously be reduced.

Placing the slide 12 in the holder 11 with the sample-bearing surface thereof facing downwardly permits the force of gravity to cause cellular components of the sample which are not electrostatically bound to the slide surface to migrate downwardly away from said surface. This substantially reduces the centrifugal forces required for separation of such components from those which are bound to the slide surface, thereby facilitating the formation of a high quality monocellular layer on the slide.

Placement of the slide 12 within the holder 11 with the sample-bearing side thereof facing downwardly also provides protection of the sample from the buffeting action of air currents generated by spinning of the holder 11 so that cell distortion and premature drying of the sample are prevented. More specifically, when the slide 11 is in the operative position shown in FIGS. 2 and 3, the slide 12, side walls 15 and 16, rails 20 and 21 and bottom wall 14 provide an open-ended enclosure preventing any substantial air flow over the surface of the sample during spinning. This is in contrast to the not completely successful prior art measures for protecting the spinning blood sample from air currents, for example by provision of an enclosure within which the slide holder is mounted for rotation. In such prior arrangement, the sample is subjected to air currents generated within the enclosure during spinning.

Preparation of monocellular layers by the method of the present invention makes unnecessary the heavy, cumbersome and expensive equipment necessary to provide the rapid acceleration, precise timing speed, and rapid deceleration employed in conventional spin techniques to prevent premature drying and cell distortion caused by buffeting of the sample by air currents.

The structure of the holder 11 is such that, during spinning, the slide 12 is firmly held in its operative position without the need for the clamps, springs or other retaining means used in prior art apparatus. Because the space within the holder 11 below slide 12 is open only at the outer ends of the slide, as the holder and slide are spun, the air pressure in the space below the slide is reduced to subatmospheric so that said slide is pressed firmly down onto the rails 20 and 21 by the higher external atmospheric pressure. This downward pressure, being centrifugally generated, is relieved when spinning is stopped, at which time the slide 12 can be readily removed from the holder 11 by digitally engaging opposite edge portions thereof at the cutaway portions 32 and 33.

Still another advantage of the structure of the improved apparatus is that it avoids any potential contamination of the atmosphere by vaporization or aerosolization of samples suspected of containing infectious components, and does so without the elaborate containment measures resorted to in some prior art apparatus. Protection of the sample from air current during spinning and collection of spun-off sample portions in the integral end wells of holder 11 prevents sample aerosol formation which could result in atmospheric contamination. The holder 11, being molded organoplastic material, is inexpensive and can be disposed of, rather than cleaned, after a number of slides have been spun therein.

The improved method makes possible the facile preparation of monocellular layers for counting in manual or in automatic differential counting (ADC) procedures. The small volume blood sample required permits preparation of ADC compatible blood smears from capillary blood at outlying collection points, such as a small group medical practice or a doctor's office, in preference to the present practice of having to draw venous samples at such locations and send them to a central laboratory for smearing and counting. The superiority of the smear produced, as well as the low cost of the improved apparatus make the improved method and apparatus attractive to those doing manual blood counts. The improved apparatus is ideally suited for transport in a phlebotomist's blood collection tray.

While the improved method and apparatus have been described with reference to the preparation of monocellular layers of blood, it will be understood that other biological fluids and suspensions, such as of tissue and bone marrow, may be similarly processed to provide monocellular layers thereof in accordance with the present invention. The apparatus shown and described herein, while presently preferred for use in practicing the improved method, is merely illustrative of the principles of the invention, and various changes and modifications may be made therein without departing from the spirit of the invention. All of such changes and modifications are contemplated as may come within the scope of the appended claims.

What is claimed as the invention is:

1. A method of producing a monocellular layer of cell-containing biological fluid on a microscope slide or the like, which method comprises the steps of depositing a sample of the fluid on a surface of a microscope slide or the like, inverting said slide so that the sample-bearing surface thereof faces downwardly, and then spinning said slide about a vertical axis normal to said surface.

2. The method of claim 1 wherein, prior to spinning, the sample is spread over said surface of the slide by the wedge technique.

3. The method of claim 1 wherein said biological fluid is blood.

4. The method of claim 1 wherein said sample is prevented from contact by buffeting air currents during said spinning.

5. The method of claim 1 wherein said slide is spun while in a holder therefor having wall means for preventing contact of said sample by buffeting air currents during said spinning.

6. The method of claim 1 wherein said slide is spun while in a holder therefor and sample portions spun off from said slide during spinning are collected in well means forming part of said holder.

7. The method of claim 1 wherein said slide is spun while in a holder therefor having wall means for preventing contact of said sample by buffeting air currents during spinning, and sample portions spun off from said slide during spinning are collected in well means forming part of said holder.

8. A method of producing a monocellular layer of a cell-containing biological fluid on a microscope slide or the like, which method comprises the steps of depositing a sample of the fluid on a surface of microscope slide or the like, and then spinning said slide about a vertical axis normal to said surface while preventing contact of said sample by buffeting air currents.

9. The method of claim 8 wherein, prior to spinning, the sample is spread over said surface of the slide by the wedge technique.

10. The method of claim 8 wherein said biological fluid is blood.

11. The method of claim 8 wherein said slide is spun while in a holder therefor having wall means for preventing contact of said sample by buffeting air currents during said spinning.

12. The method of claim 8 wherein said slide is spun while in a holder therefor and sample portions spun off from said slide during spinning are collected in well means forming part of said holder.

13. The method of claim 8 wherein said slide is spun while in a holder therefor having wall means for preventing contact of said sample by buffeting air currents during said spinning, and sample portions spun off from said slide during spinning are collected in well means forming part of said holder.

* * * * *